United States Patent [19]

Lessar et al.

[11] Patent Number: 4,947,866
[45] Date of Patent: Aug. 14, 1990

[54] MEDICAL ELECTRICAL LEAD

[75] Inventors: Joseph F. Lessar, Coon Rapids; Duane L. Rosenberg, Columbia Heights; Robert E. Kraska, Minneapolis; James M. Speckien, Vadnais Hts.; James E. Upton, New Brighton, all of Minn.

[73] Assignee: Medtronic, Inc., Minneapolis, Minn.

[21] Appl. No.: 354,656

[22] Filed: May 19, 1989

Related U.S. Application Data

[62] Division of Ser. No. 156,145, Feb. 16, 1988, Pat. No. 4,860,446.

[51] Int. Cl.$^5$ .............................................. A61N 1/05
[52] U.S. Cl. ...................................... 128/784; 128/786
[58] Field of Search ............... 128/784, 783, 786, 642, 128/78 S, 419 P

[56] References Cited

U.S. PATENT DOCUMENTS

| | | | |
|---|---|---|---|
| 3,348,548 | 10/1967 | Chardack | 128/418 |
| 3,788,329 | 1/1974 | Friedman | 128/418 |
| 4,269,198 | 5/1981 | Stokes | 128/785 |
| 4,328,812 | 5/1982 | Ufford et al. | 128/786 |
| 4,573,473 | 3/1986 | Hess | 128/642 |
| 4,602,637 | 7/1986 | Elmqvist et al. | 128/419 P |
| 4,640,983 | 2/1987 | Comte | 128/784 |
| 4,644,957 | 2/1987 | Ricciardelli et al. | 128/642 |
| 4,677,989 | 7/1987 | Robblee | 128/419 P |
| 4,679,572 | 7/1987 | Baker, Jr. | 128/785 |

FOREIGN PATENT DOCUMENTS

| | | | |
|---|---|---|---|
| 1146228 | 5/1983 | Canada | 337/70 |
| 3300668 | 7/1984 | Fed. Rep. of Germany | 128/784 |
| 8004757 | 2/1981 | Netherlands | 128/784 |
| WO85/00462 | 1/1985 | PCT Int'l Appl. | |

OTHER PUBLICATIONS

Article entitled "New Test Methods for the Evaluation of Stress Cracking and Metal Catalyzed Oxidation in Implanted Polymers", by Stokes et al., published in *Polyurethanes in Biomedical Engineering II*, Proceedings of the 2nd International Conference on Polyurethanes in Biomedical Engineering, 1987.

Article "The Electrode-Biointerface: Stimulation", Chapter 3 of *Modern Cardiac Pacing*, edited by Barold, 1985.

*Primary Examiner*—Lee S. Cohen
*Assistant Examiner*—S. Getzow
*Attorney, Agent, or Firm*—Reed A. Duthler; Joseph F. Breimayer

[57] ABSTRACT

A medical electrical lead having a polyurethane outer sheath and one or more coiled metal conductors. The metal conductors are optimized for use in conjunction with a polyurethane sheath and are provided with a barrier coating of a biocompatible metal. The conductors may additionally be provided with an outer, insulative coating.

4 Claims, 3 Drawing Sheets

MEDICAL ELECTRICAL LEAD

This is a divisional of co-pending application Ser. No. 156,145, filed on Feb. 16, 1988, now U.S. Pat. No. 4,860,446.

BACKGROUND OF THE INVENTION

This invention relates generally to implantable electrical leads, and in particular to electrical stimulation leads.

In the early days of pacing, a cardiac pacing lead was viewed simply as a wire connecting the pacemaker to the heart. However, those skilled in the art have come to appreciate that a cardiac pacing lead as implanted is part of a complicated electrical, mechanical and chemical system.

In an effort to improve performance, manufacturers of pacing leads have selected specific commercially available alloys which have particularly advantageous mechanical and electrical properties when used in pacing leads. These include stainless steels, Elgiloy ® alloy, MP35N alloy, and DBS/MP. DBS is a drawn-brazed-strand, having a silver core surrounded by strands of stainless steel or of MP35N alloy. All of these conductors, when coiled, display appropriate mechanical and electrical characteristics for use in electrical stimulation leads.

Although most early pacing leads were fabricated using silicone rubber to insulate the conductors, manufacturers have become aware of the superior mechanical properties of commercially available polyether urethanes. These include Pellethane 80A and Pellethane 55D polyurethanes manufactured by Dow Chemical Company. These polyurethanes are less thrombogenic than silicone rubber and higher in tensile strength. In addition, they slide easily against one another when moistened with body fluids. This property facilitates the use of two leads in a single vein, which was difficult with the older silicone rubber bodied leads. Unfortunately, recent experience has suggested that cobalt, chromium and molybdenum, commonly used in lead conductors, may accelerate oxidative degradation of polyurethanes used in pacing leads. MP35N, Elgiloy and DBS/MP all include cobalt, molybdenum and chromium as significant constituents. To a lesser degree, it appears that stainless steels may also accelerate polyurethane degradation.

An additional set of improvements in implantable electrical leads has been the trend toward fabrication of multiconductor coils, rather than separate, mutually insulated coils. Early leads, such as those disclosed in U.S. Pat. No. 3,348,548 and U.S. Pat. No. 3,788,329 show separate conductor coils in a side by side or coaxial configuration, insulated from one another by sheaths covering the entirety of the coils. More recently, multipolar coiled conductors having individually insulated coil wires have been pursued, as disclosed in Canadian Pat. No. 1,146,228, for a Multipolar Pacing Conductor, issued May 10, 1983 to Upton. This patent discloses a single, multiconductor DBS coil having individually insulated wires, appropriate for use in conjunction with a polyurethane outer insulation and is incorporated herein by reference in its entirety.

SUMMARY OF THE INVENTION

The present invention is directed toward an optimal construction for a pacing lead or other medical electrical lead of the type having a conductor wire including a transition metal which accelerates polyurethane degradation and having polyetherurethane insulative sheathing. Cobalt, chromium, and molybdenum are three examples of such transition metals. Other transition metals including iron are also believed to accelerate polyurethane degradation. By coating the conductor wire with an inert material such as platinum, titanium, niobium or tantalum, which does not interact with polyurethane, a chemically stable lead configuration is produced. By providing an extremely thin coating of the inert metal, the desirable mechanical characteristics of the basic materials used in lead conductor wires are retained. Preferably, the coating is limited to a coating no more than 200 microns in thickness. The coating may also be provided by a sputtering technique which can produce an extremely thin coating, but still functional, of less than 1000 angstroms in thickness. This thinner coating is advantageous because it does not alter the mechanical characteristics of the wire.

DETAILED DESCRIPTION OF THE INVENTION

Figure 1:
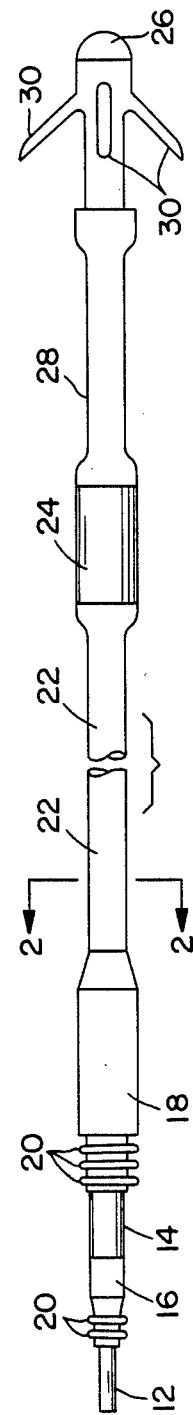
FIG. 1 is a plan view of a bipolar pacing lead according to the present invention.

FIG. 1 shows a plan view of a cardiac pacing lead according to the present invention. The pacing lead 10 includes a connector assembly at its proximal end, including a first conductive surface 12, a second conductive surface 14, and two insulative segments 16 and 18. Insulative segments 16 and 18 are each provided with a plurality of sealing rings 20. Extending from the connector assembly is an elongated lead body, including an outer insulative sheath 22, which is preferably fabricated of polyurethane. Appropriate polyurethanes include Pellethane 80A and Pellethane 55D, both products of Dow Chemical Co. Within insulative sheath 22 is located a quadrifilar, multiconductor coil. Two of the conductors within the coil are coupled to conductive surface 12. The other two are coupled to conductive surface 14. Although the embodiment illustrated in FIG. 1 employs a bipolar, quadrifilar coil, the conductor wires described herein may also be used advantageously in unipolar leads and in leads employing coils having three or more mutually insulated conductors.

At the distal end of the lead are located a ring electrode 24, coupled to two of the conductors, and a tip electrode 26, coupled to the other two of the four conductors of the quadrifilar coil. Extending between ring electrode 24 and tip electrode 26 is an additional polyurethane sheath 28. Fixation of the electrode within the heart is assisted by a plurality of flexible tines 30, as described in U.S. Pat. No. 3,902,501, issued to Citron et al. Tines 30 may be fabricated of polyurethane or silicone rubber.

Figure 2:
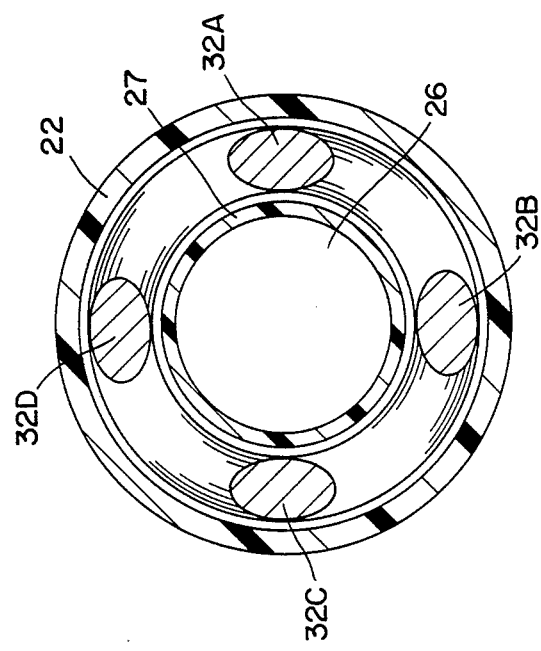
FIG. 2 is a cross sectional view of the lead of FIG. 1.

FIG. 2 shows a cross section through the lead of FIG. 1, intermediate the connector assembly and the ring electrode 24. In this view, the quadrifilar coil within sheath 22 is visible. This coil consists of four individual conductors 32A, B, C and D. The multifilar coil is provided with an internal lumen 26, which allows for the passage of a stylet. A Teflon ® plastic liner 27 within lumen 26 may be provided to protect conductors 32A, B, C and D from nicks that might otherwise occur due to passage of the stylet.

Figure 3:
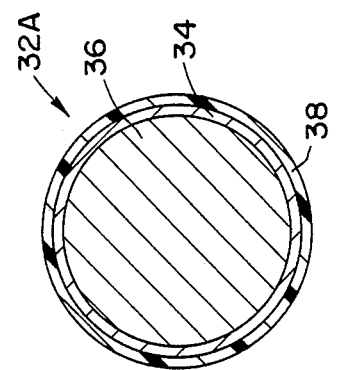
FIG. 3 is a cross sectional view through one of the conductor wires used in a lead according to FIG. 1

FIG. 3 shows a cross section of one of the individual conductors of the coil, 32A. Conductor 32A consists essentially of a core 28 fabricated of an alloy such as MP35N or Elgiloy ® alloy or fabricated of DBS. The outer surface of conductor 32A is coated with a thin coating of an insulative, flexible polymer 38. Polymer coating 38 is preferably Tefzel ® fluorocarbon coating manufactured by Dupont. Coating 38 is preferably applied using an extrusion process. Other appropriate insulative coatings, including Teflon ®, plastic, polyurethanes and polyamids, may also be used.

Intermediate coating 38 and core 36 is a thin layer 34 of an inert body compatible metal, free of cobalt, molybdenum and other materials which negatively interact with polyether urethanes. Preferably, this layer consists of platinum, niobium, tantalum, titanium or alloys thereof, such as a platinum/niobium alloy. Other biocompatible metals, which are inert when in body fluids and in contact with polyurethanes may also be appropriate substitutes. An appropriate process for providing coating 34 is a sputtering process as set forth below. This process preferably is employed to provide a coating of between 300–500 Å.

Figure 4:
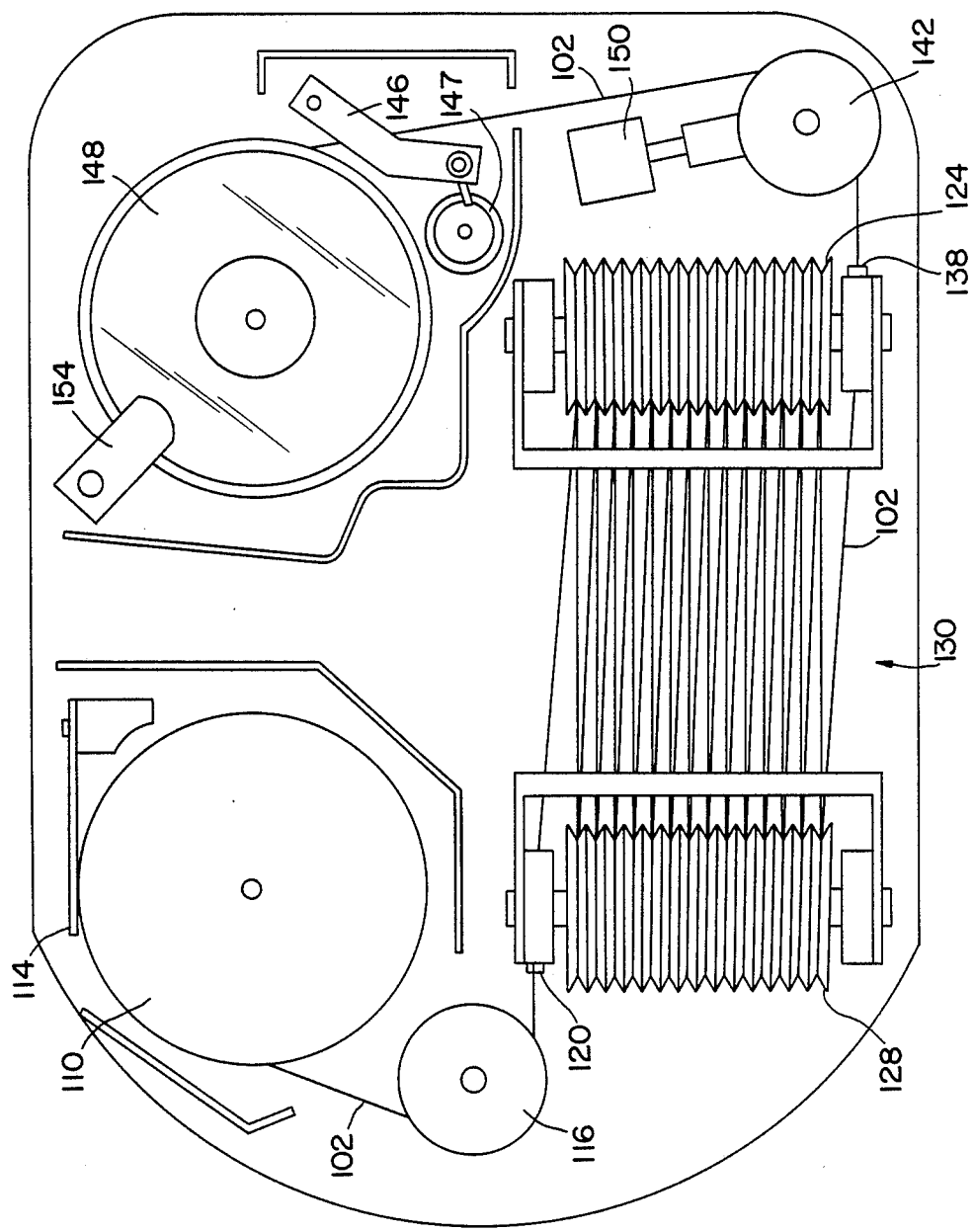
FIG. 4 is a top plan view of a wire transport used in sputtering conductor wires.

FIG. 4 illustrates a top plan view of a wire transport apparatus useful for sputter coating conductor wire according to the present invention. Wire 102 is initially loaded onto payoff reel 110. Payoff reel 110 is provided with a drag 114 which maintains wire tension. The wire 102 then passes to idler pulley 116, through wire guide 120 and then onto grooved spool 124. There is also provided a second grooved spool 128. The wire 102 is wound between the grooved spools 124 and 128 so that it makes a plurality of passes across the process area 130. By providing for multiple passes through the process area, the wire transport mechanism allows for much more rapid processing of the wire than would a single pass system.

The wire 102 comes off of grooved spool 128 and passes through wire guide 138 to the idler pulley 142 and then to level winder 146. The level winder 146 is operated by means of cylindrical cam 147. The wire is taken up by the take-up spool 148 which is motor driven. In the embodiment illustrated, the take-up spool 148 is conductive, but insulated from the rest of the wire transport, as is wire 102. A negative bias may be applied to take-up spool 148 by means of contact 154.

The transport of FIG. 4 is intended for use with a sputtering cathode mounted horizontally above the process area 130. However, the arrangement of the transport mechanism may vary from that shown. For example, the grooved spools 124 and 128 may be mounted vertically and the magnetron cathode and anode also mounted vertically. This alternative arrangement allows for the use of two cathodes, one on either side of the grooved spools. In addition, by duplicating the parts of the wire transport, sputtering of two or more wires simultaneously may be accomplished. Regardless of the specific configuration chosen, it is important that the wire's path does not include any bends or exposure to sharp edges which would damage the wire or alter its mechanical properties. It is desirable to employ a tension monitor along the wire path in order to detect breaks or other malfunctions of the wire transport system. In the device of FIG. 4, the tension monitor 150 is coupled to idler pulley 142.

FIG. 4 is intended only as one example of a usable wire transport system. Other systems, such as that illustrated in PCT Patent Application PCT/GB84/00246, International Publication No. WO85/00462, might also be utilized.

Figure 5:
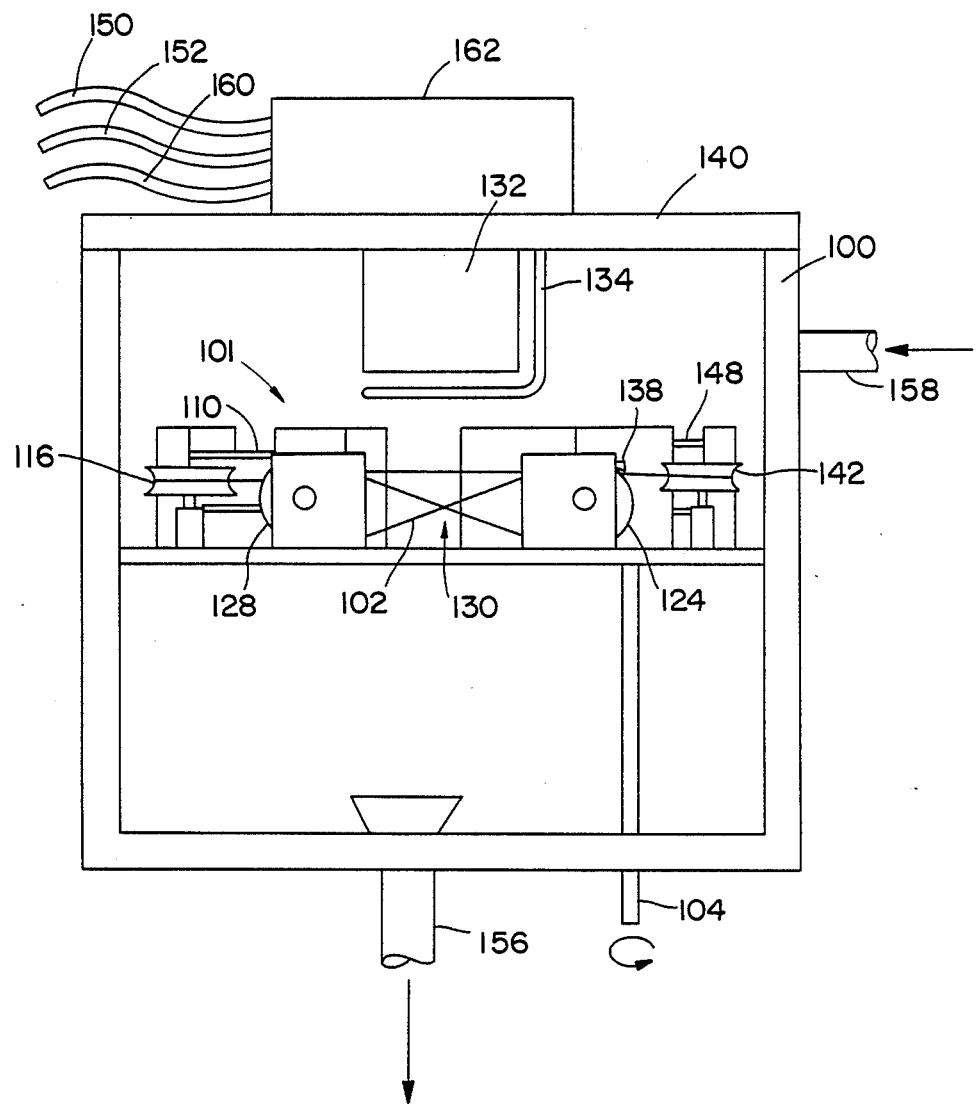
FIG. 5 is a side, cutaway view of an apparatus for sputtering conductor wires.

FIG. 5 is a side, cutaway view of the assembled apparatus for sputtering conductor wire. The illustrated device employs a magnetron sputtering process, in which plasma of an inert gas, such as argon, is generated by means of an electric field. The apparatus employs a bias sputtering technique in which the wire conductor may be held at a negative potential relative to the vacuum chamber and plasma. A discussion of this type of sputtering as applied to the coating of wires is contained in PCT Patent Application No. PCT/GB84/00246, published Jan. 31, 1985, as International Publication No. WO85/00462 for "Wire and Cable", by O'Brien et al. This published application is incorporated herein by reference in its entirety. This application also discloses alternative methods of wire coating which may also be advantageously employed in providing an inert metal coating on a conductor according to the present invention. These methods include RF sputtering, evaporative coating, activated evaporation, ion plating, and plasma assisted chemical vapor deposition.

The apparatus illustrated in FIG. 5 is adapted for batch sputtering of wire conductor, and includes a vacuum chamber 100 which contains the complete wire transport mechanism 101. In this view, the criss-cross pattern of wire 102 intermediate the grooved spools 124 and 128 is visible. Shaft 104 which drives take-up reel 148 is also visible. The magnetron cathode 132 and anode 134 are mounted to the removable top 140 of vacuum chamber 100. Cooling lines 150, 152 and power cable 160 are routed to the magnetron cathode 132 via housing 162. In the specific embodiment employed by the inventors, a 4 inch D.C. magnetron cathode, Type C, manufactured by Vac-Tec Systems is used. For best results, the wire 102 should pass within 3 or 4 inches of the cathode 132. The target which comprises the metal to be sputtered is mounted to cathode 132. Vacuum is applied to the chamber by means of vacuum port 156. Argon gas is supplied to the chamber by means of gas port 158.

The thickness of the coating provided by the apparatus of FIG. 5 is dictated by a combination of factors, including distance to target, argon gas pressure, wire speed, number of passes and magnetron power setting. In general, it has been found that a coating rate of approximately 1000 Angstroms per minute provides an adequate coating. However, other coating rates may be used. Preferably, a layer of about 500 Å or less is deposited. The apparatus illustrated in FIG. 5 is useful in depositing platinum, tantalum, niobium and titanium, as well as other materials.

The general operation of the device of FIG. 5 to provide a sputtered platinum coating on MP35N alloy or DBS wire of about 0.1 to 0.3 mm in diameter is as follows. After loading the wire onto the wire transport system, the vacuum chamber 100 is evacuated to about $5 \times 10^{-7}$ Torr and the cooling system for the magnetron cathode 132 is activated. After pressure has stabilized, argon gas is admitted via gas port 158, with gas pressure in the chamber regulated to about 2 milliTorr. The magnetron 132 is then activated in its DC mode, and adjusted to a power output of approximately 0.5 kilowatts. After the power level stabilizes, the motor driving take-up reel 148 is activated, and a negative bias may be applied to take-up reel 148. Bias voltages from 0 to negative 100 volts result in satisfactory coatings. Wire transport speed should be adjusted to provide the desired coating thickness. These parameters will of course vary depending upon the number, type, and arrangement of sputtering cathodes employed.

It has been found that proper cleaning of the wire prior to sputtering enhances the deposition and adhesion of the sputtered material. One satisfactory method of cleaning the wire is to sequentially pass the wire through cleaning baths such as trichloroethane, isopropyl alcohol, a mild alkali based detergent solution, deionized water, isopropyl alcohol and freon, in that order. The solvents may be contained in ultrasonic cleaners, with the exception of the freon. The wire should stay immersed in each solvent for long enough to assure thorough cleaning. A time of 2-3 minutes has been found to be adequate. Vapor degreasing systems such as disclosed in the above-cited PCT application are also believed appropriate.

When used in leads having multiconductor coils, it is expected that at least some of the wires will be provided with a layer of insulating material in order to provide electrical isolation of the individual conductors in the coil. However, in unipolar leads and other leads not employing multiconductor coils, the coated wire may be used without an insulative layer. In either embodiment, the metal coated wire provides significant advantages. In embodiments not employing an outer insulative layer, niobium, tantalum and titanium are believed especially preferable.

Conductor wires produced according to the present invention are believed particularly advantageous for use in cardiac pacing leads. Testing by the inventors has indicated that pacing leads employing polyurethane insulation and conductor wires coated using the process described above have a substantially increased resistance to oxidative degradation compared to similar leads having uncoated conductor wires. For this testing, the insulative layer was omitted.

As used in pacing leads, conductor wires are typically less than 0.25 mm in diameter, and are wound into extremely small diameter coils, having diameters of 3 mm, or less and typically 2 mm or less. With sputter coated wire, winding of coil sizes appropriate for use in pacing leads causes the sputtered coating to develop small breaches or cracks. However, simply covering a high percentage of the surface area of the conductor provides substantial improvement in resistance to oxidative degradation of the polyurethane sheath. Moreover, the inventors have determined that actual physical contact between the conductor and the polyurethane insulation is a significant factor in the oxidative degradation of the polyurethane insulation. Even in the absence of an insulative outer layer, the typical cracks and breaches in the sputtered coating due to winding are unlikely to produce significant areas of contact between the base metal of the coil and the polyurethane insulation.

The importance of actual physical contact between the conductor base metal and the polyurethane leads to another surprising result. The inventors have determined that a prewound conductor coil, sputtered using the method and apparatus described above, and not employing an outer, insulative layer, still provides a substantial increase in resistance to oxidative degradation of the polyurethane sheath. Although the innermost portions of the coil will not be covered by the sputtered coating, the outer portion of the coil which will directly contact the polyurethane insulation will be coated, and this appears to be sufficient.

Although the specific embodiment disclosed in the present application is a cardiac pacing lead, the teaching of the application and the claims hereof are believed equally applicable to other implantable electrical leads, such as neurostimulation leads or leads employing electrical transducers. In addition, in embodiments employing a single electrode, using either a monofilar coil or a unipolar, multifilar coil, the polymer coating 38 may be dispensed with entirely.

In conjunction with the above description, we claim:

1. A medical electrical lead comprising:
   an elongated insulative sheath fabricated of a polyether urethane;
   an elongated coiled conductor, located within said polyether urethane sheath;
   an electrode coupled to a distal end of said elongated coiled conductor; and
   an electrical connector coupled to a proximal end of said elongated conductor; and
   wherein said elongated coiled conductor comprises a coiled wire of a first alloy including cobalt, molybdenum or chromium, provided with a coating of a second metal selected from the group consisting of platinum, titanium, niobium or tantalum.

2. A lead according to claim 1 wherein said coating of said second metal is 200 microns or less in thickness.

3. A lead according to claim 1 wherein said coating of said second metal is about 500 angstroms or less in thickness.

4. A medical electrical lead, comprising:
   a multifilar coil conductor;
   an elongated insultive sheath encasing said multifilar coil conductor, said insulative sheath fabricated of polyether urethane; and
   at least one electrode coupled to a distal end of at least one of the filars in said multifilar coil conductor; and
   wherein said multifilar coil conductor comprises a plurality of wires fabricated from an alloy containing cobalt, molybdenum or chromium, and provided with a coating of a second, bicompatible inert metal selected from the group consisting of titanium, platinum, niobium, tantalum, and alloys thereof, said wires further provided with an outer coating of an insulative material whereby the individual filars of said multifilar coil conductor are electrically insulated from one another.

* * * * *